United States Patent [19]

Creswick

[11] 3,999,421
[45] Dec. 28, 1976

[54] POWDER BULK DENSITY INSTRUMENT

[75] Inventor: Norman S. Creswick, Wyckoff, N.J.

[73] Assignee: Thomas J. Lipton, Inc., Englewood Cliffs, N.J.

[22] Filed: Oct. 6, 1975

[21] Appl. No.: 620,246

[52] U.S. Cl. .............................................. 73/32 A
[51] Int. Cl.² ....................................... G01N 9/00
[58] Field of Search ......................... 73/32 A, 32 R

[56] References Cited

UNITED STATES PATENTS

| | | | |
|---|---|---|---|
| 2,943,476 | 7/1960 | Bernstein | 73/32 A |
| 3,021,711 | 2/1962 | Arvidson | 73/398 R |
| 3,218,851 | 11/1965 | Sipin | 73/32 A X |
| 3,444,723 | 5/1969 | Wakefield | 73/32 A |
| 3,504,526 | 4/1970 | Banks | 73/32 A |
| 3,516,283 | 6/1970 | Abbotts | 73/30 |
| 3,583,209 | 6/1971 | Banks | 73/32 A |
| 3,608,374 | 9/1971 | Miller | 73/194 B |
| 3,665,752 | 5/1972 | Piper | 73/32 A |
| 3,763,692 | 10/1973 | Agar | 73/32 A |

Primary Examiner—James J. Gill
Attorney, Agent, or Firm—Brumbaugh, Graves, Donohue & Raymond

[57] ABSTRACT

A continuous, in-line bulk density instrument is described which provides real time monitoring of a product stream consisting of a free flowing powder. The instrument utilizes a cylindrical tube pendulum whose period of oscillation is measured to determine the bulk density of the powder flowing therethrough.

17 Claims, 11 Drawing Figures

FIG. 1
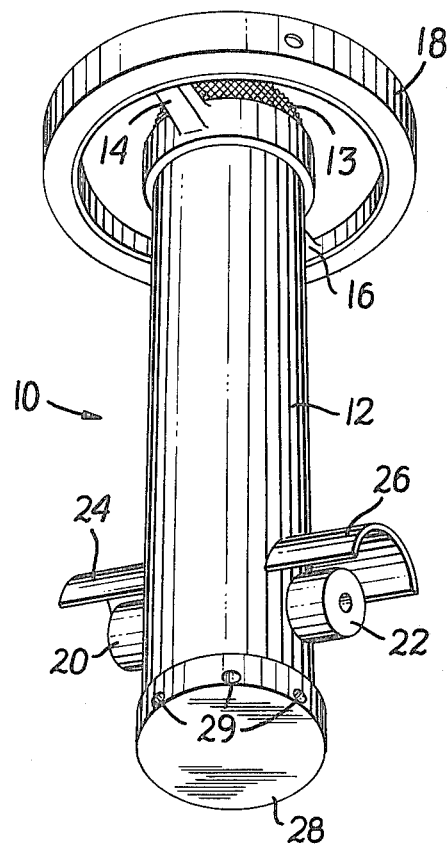
FIG. 2
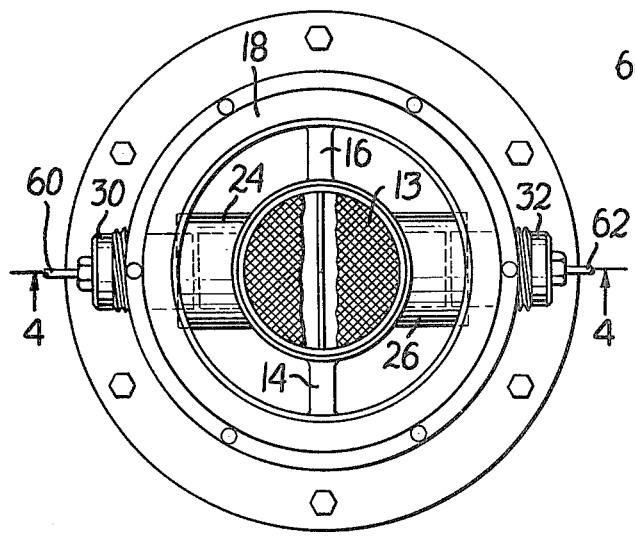
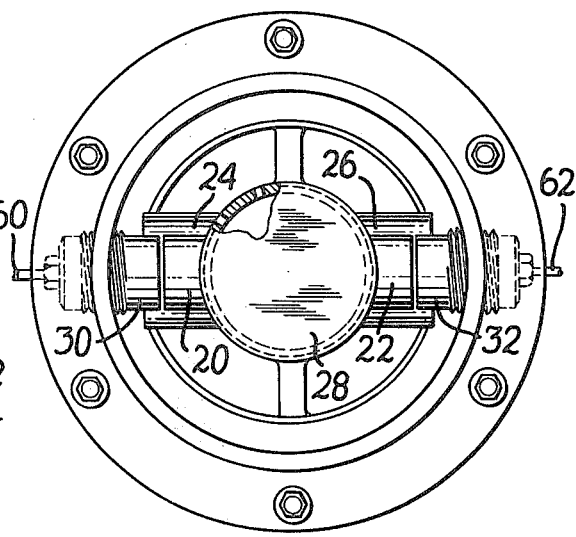
FIG. 3

FIG. 7
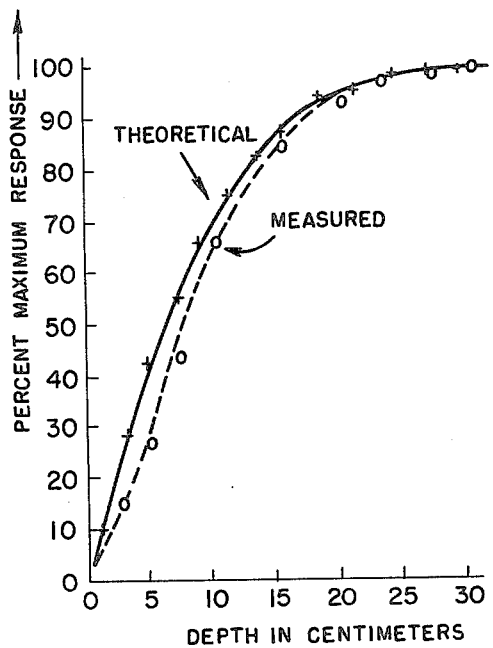
FIG. 9
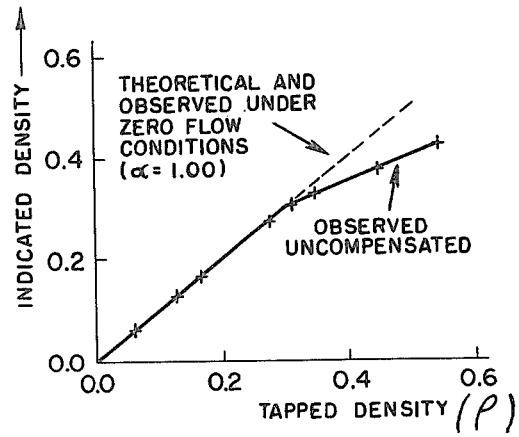
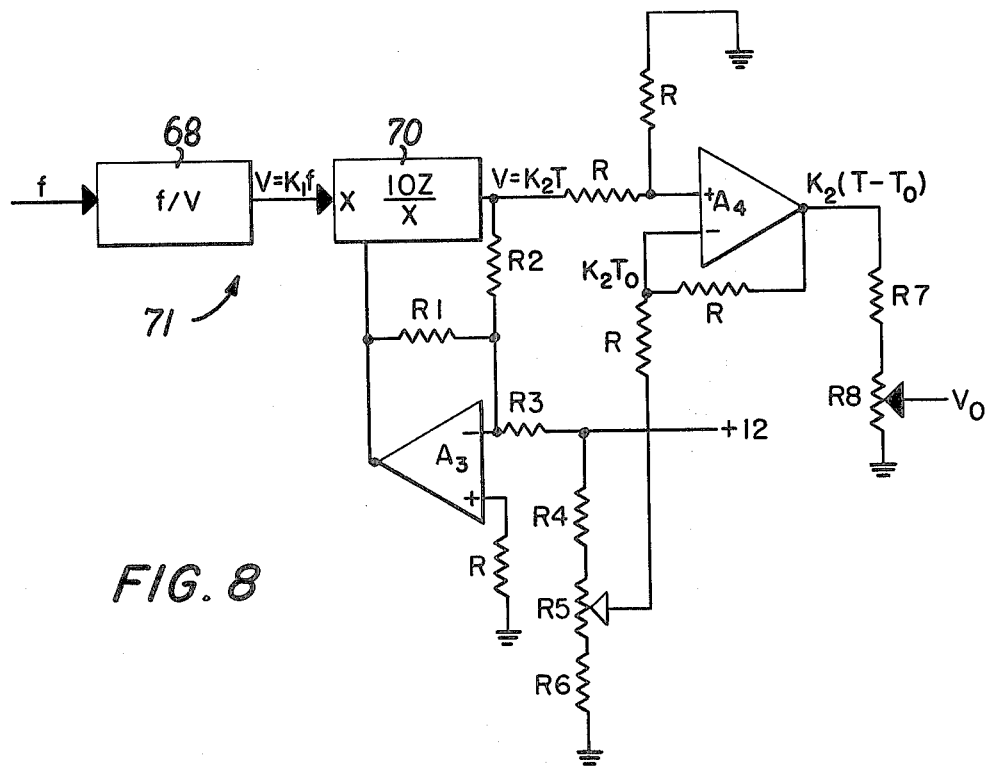
FIG. 8

POWDER BULK DENSITY INSTRUMENT

BACKGROUND OF THE INVENTION

The present invention relates to an in-line powder bulk density measuring instrument.

In a manufacturing process powder bulk density is conventionally monitored by tapping a sample of the product stream under standardized conditions and calculating the ratio of mass to volume from the observed results. The conventional measurement techniques are reasonably accurate for particular samples, but they leave much to be desired in view of the hiatus between the time the sample is obtained from the product stream and the time the density is determined. During this time, which may be on the order of ten minutes in the manufacture of powdered tea, product continues to be made, possibly with the wrong bulk density.

Ideally, bulk density should be measured in zero time. In the past, this could not be achieved because the physical process involved in compacting a powder to its "tapped density" or minimum volume state inherently involves time.

The problem of measuring "tapped density" involves the measurement of mass, the definition of volume, and the establishment of well-defined energy-time input conditions.

SUMMARY OF THE INVENTION

It has now been found that an instrument for measuring the bulk density of a stream of free flowing powder may be provided by using, in combination, a cylindrical body substantially open at the top and bottom and adapted to receive and discharge a stream of powder; mounting means for suspending said body in a substantially vertical position, said mounting means attached to allow said body to oscillate in a vertical plane about said mounting means; driving means for causing said body to oscillate in said vertical plane; measuring means for determining the oscillation period of said body, which period varies with the density and amount of material in the apparatus; and at least one spring adapted to generate a restoring force upon said body when said body is pivoted about said mounting means. The driving means may comprise at least one magnet attached to the cylindrical body and preferably at least one drive electromagnet. The measuring means preferably comprises at least one pickup electromagnet adapted to have a voltage induced therein by at least one magnet mounted on the cylindrical body.

The instrument also preferably includes servo drive means for inducing a voltage in the drive electromagnet means of the driving means in response to the voltage induced in the pickup electromagnet.

In a preferred embodiment, the opening of the cylindrical body is covered by a protective screen and the bottom of the body is partially closed to restrict the flow of powder through said body. In each embodiment, the readout flow of the powder is measured by a measuring means which comprises an electronic circuit responsive to the frequency of oscillation of said body and whose output is a signal representative of the density of the material in said body.

The apparatus of the present invention embodies the concept of a torsional pendulum to provide the required energy input and enable the simultaneous measurement of mass via the natural period of the pendulum. This geometry allows the instrument to be coaxial; the device may be mounted in a product stream and excess product permitted to flow around the torsional pendulum operating within a large pipe. By appropriate choice of dimensions of pipe and apparatus, the annular area is made equal to the product stream pipe area thus minimizing restriction of flow of the product through the pipe.

In those instances where it is necessary to include a temperature compensating factor in the determination of the bulk density of the material being measured, a temperature probe is positioned at an appropriate point in the stream of flowing powder immediately adjacent the density instrument of the present invention. The signals from the temperature probe are used to make appropriate corrections in the readout as will be explained in more detail infra.

The following discussion relates to the theory of the present invention.

If a pendulum constructed of a rigid, massless, hollow cylinder is filled with powder and supported at its upper end by a torsional spring connected at right angles to the axis of motion, application of the parallel axis theorum yields:

$$I_p = \rho V L^2 \left[ \left( \frac{R^2}{4L^2} + 1 \right)\left(\frac{h}{L}\right) - \left(\frac{h}{L}\right)^2 + \frac{1}{3}\left(\frac{h}{L}\right)^3 \right] \quad \text{Eq. (1)}$$

Where:
 $I_p$ = moment of inertia of powder
 $V$ = volume of cylinder
 $\rho$ = mass per unit volume of powder
 $R$ = inside radius of hollow cylinder
 $L$ = length of hollow cylinder
 $h$ = depth of powder measured from the bottom of the cylinder Eq. (1) may be reduced to Eq. (2) when $h = L$:

$$I_p = \frac{\rho V L^2}{3} + \frac{\rho V R^2}{4} \quad \text{Eq. (2)}$$

Omitting the small contribution of the second term, Eq. (2) simplifies to:

$$I_p = \frac{\rho V L^2}{3} \quad \text{Eq. (3)}$$

Analysis of the pendulum when empty, and taking into account its effective mass, yields:

$$T_0 = 2\pi \sqrt{\frac{I_0}{K}} \quad \text{Eq. (4)}$$

Where:
 $T_0$ = natural period of oscillation when empty
 $I_0$ = moment of inertia of moving mass
 $K$ = spring constant of torsional spring For the case where the cylinder is full of powder:

$$T = 2\pi \sqrt{\frac{I_0 + I_p}{K}} \qquad \text{Eq. (5)}$$

Where $T$ = natural period of oscillation when full.

Division of Eq. (5) by Eq. (4) and combining with Eq. (3) yields:

$$T = T_0 \sqrt{1 + K'\rho} \qquad \text{Eq. (6)}$$

Where $$K' = \frac{VL^2\alpha}{3I_0}$$

and $\alpha$ is the ratio of effective density to the maximum density of the powder contained within the cylinder.

Under zero flow conditions, i.e., when the cylinder is filled with powder which is not allowed to leave the system, a $\alpha$ asymptotically approaches 1.00 with time. If the powder is allowed to leave the system at the bottom, and is constantly replaced at the top, the value of $\alpha$ generally depends upon the effective residence time of the system. The effective residence time of the system, therefore, represents a boundary condition which limits the lowest response time that can be achieved under dynamic conditions. As shown by FIGS. 5 and 6, in the case of instant tea powders, $\alpha$ is a continuous well-defined function, so that $\alpha$ values in the range of 0.80 to 0.95 can be utilized to minimize response time, while allowing system calibration as though $\alpha$ were equal to 1.00.

Examination of the relationship between "$I_p$" as a function of powder depth $h$, Eq. (1), and T as a function of $I_p$, Eq. (5), indicates that the last 10% to 20% of powder depth produces only slight changes in the natural period T. This property of the torsional pendulum, as shown in FIG. 7, is fortuitous since it implies the formation of a "virtual surface" somewhere below the axis of the torsional spring. The existence of this "virtual surface" tends to establish a precisely defined volume as required by the "tapped density" boundary condition.

By rearranging the terms of Eq. (6), the relationship between the period of oscillation T and density "$\rho$" can be expressed as follows:

$$\rho = \frac{(T - T_0)(T + T_0)}{K'T_0^2} \qquad \text{Eq. (7)}$$

Eq. (7) indicates that the conversion of the period to density involves taking the difference between two relatively large numbers. Since present production standards for instant tea are $\pm 0.01$ gm/cc allowable deviation, measurements of this difference should be accurate to $\pm 1 \times 10^{-4}$ gm/cc or 1 part in 10,000. This level of performance is not easily achieved by analogue techniques, which can be used for resolutions an order of magnitude less ($\pm 0.001$ gm/cc).

BRIEF DESCRIPTION OF THE DRAWINGS

FIG. 1 is a perspective view of the body of the bulk density measuring instrument;

FIG. 2 is a top, partially broken, view of the body;

FIG. 3 is a bottom, partially broken, view of the body;

FIG. 7 is a graph showing the relationship between the period of the torsional pendulum of the body and the depth of powder within the body establishing the basis for a "virtual surface";

FIG. 8 is a schematic diagram of the readout circuitry used to determine the bulk density;

FIG. 9 is a graph showing the relationship between the actual tapped density and the density indicated by the instrument;

DETAILED DESCRIPTION OF THE PREFERRED EMBODIMENT

Figure 5:
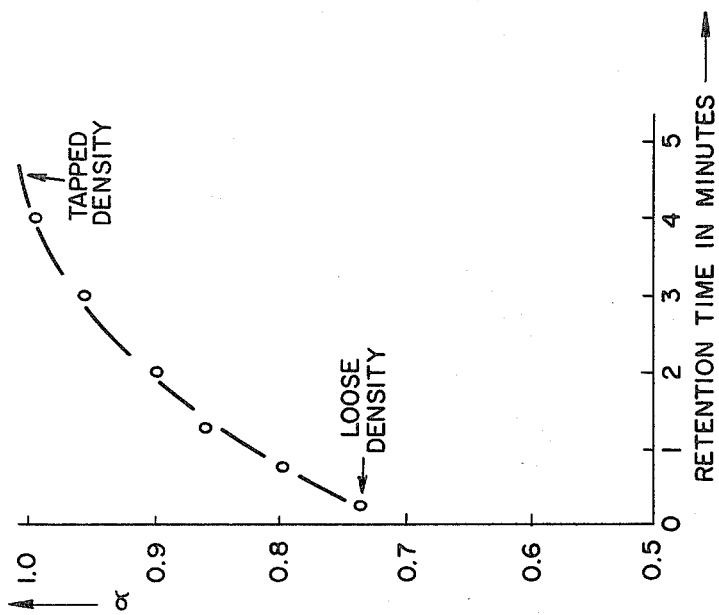
FIG. 5 is a graph showing the relationship between $\alpha$ and retention time of a powder within the body.
Figure 6:
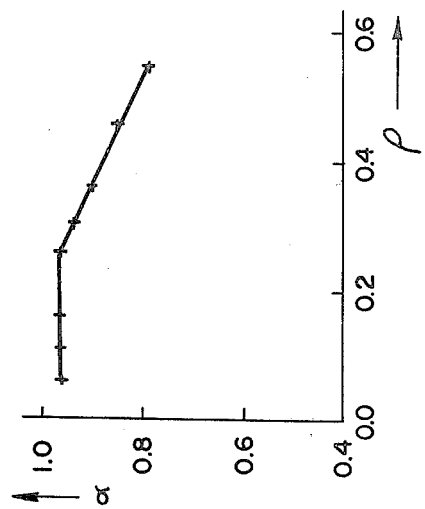
FIG. 6 is a graph showing the relationship between $\alpha$ and $\rho$.

Referring generally to FIGS. 1 through 4, the powder bulk density instrument 10 of the present invention is shown. The instrument 10 comprises a substantially cylindrical hollow body 12, closed at the top by a screen 13 and at the bottom by a cap 28 having holes 29 therethrough. The body 12 is suspended from a pair of torsion springs 14, 16 affixed between the top of the body 12 and an annular mounting bracket 18. Adjacent the bottom of the body 12 there are mounted a drive magnet 20 and a pickup magnet 22. The magnets are substantially cylindrical and extend outward from the body 12. Above and partially surrounding each magnet, there is a magnetic gap shield 24, 26, the purpose of which is to prevent powdered product from filling the gap between the magnets 24, 26 and a pair of electromagnets 30, 32 used for driving and pickup respectively.

The bottom portion of the body 12 is partially closed off by the cap 28 to partially restrict the flow of powdered product through the body 12. The top of the body 12 has a protective screen 13 thereon which prevents large, coagulated product from entering the body 12 and clogging the holes 29.

Figure 4:
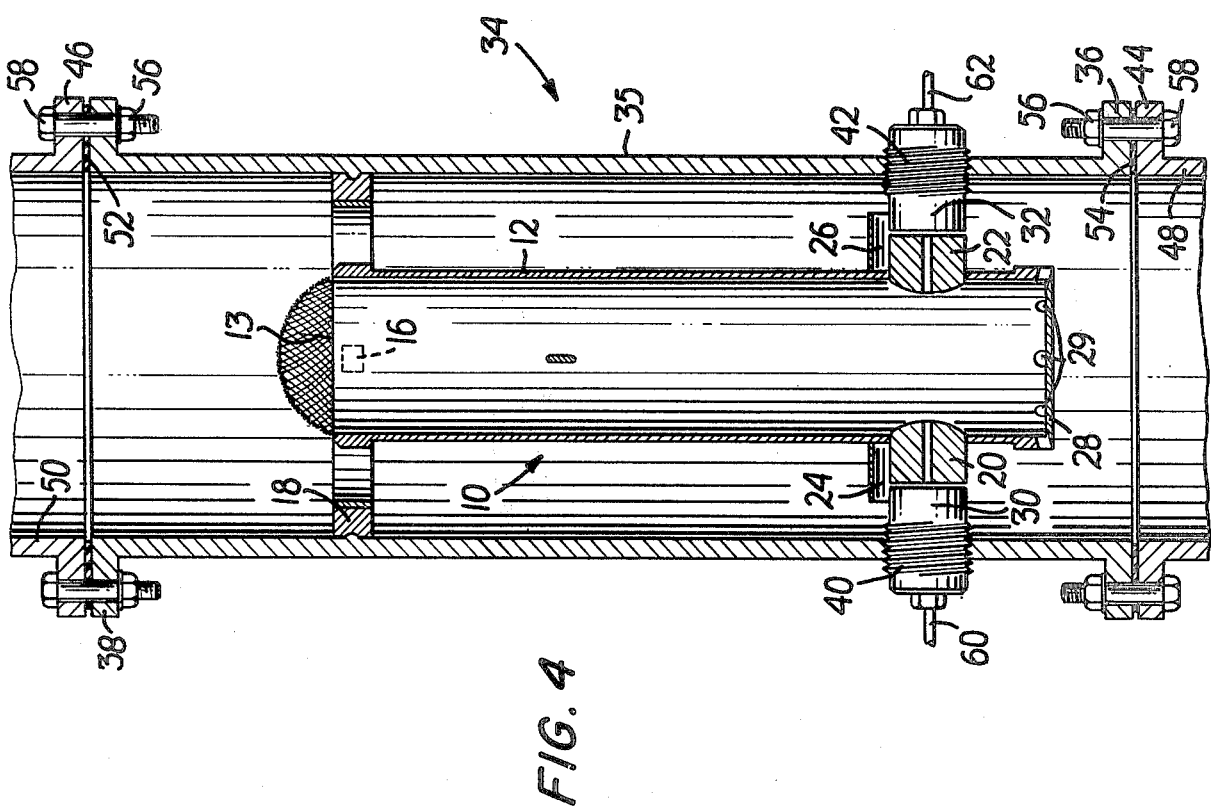
FIG. 4 is a broken side view of the body mounted in a housing taken along the line 4—4 of FIG. 2.

Referring generally to FIGS. 2 through 4, the instrument 10 is mounted in a cylindrical housing 34 having flanges 36, 38 at either end. The housing 34 allows the instrument 10 to be placed in the product stream of a powder whose bulk density is to be measured. The annular mounting bracket 18 is secured to the interior portion of the housing 34 which has an inner diameter adapted to be joined to the annular mounting bracket 18. The electromagnets 30, 32 each have a threaded portion 40, 42, respectively, which is adapted to be threaded through the wall 35 of the housing 34.

In operation, the housing 34 is mounted in the product stream of the powder whose bulk density is being measured by joining the flanges 36, 38 to suitable flanges 44, 46 in pipes 48, 50 which convey the powdered product. In joining the housing 34 to the pipes 48, 50, it is preferable to make use of gaskets 52, 54 together with suitable fastening means such as nuts 56 and bolts 58 in the standard manner.

Electrical lines 60, 62 are connected to the driving and pickup electromagnets 30, 32, respectively. In operation, product flows through the screen 13 and fills the body 12. As product flows out of the body 12 through the holes 29 in the cap 28, new product enters the top opening through the screen 13. A signal is imposed on the drive coil 30 through input line 60. The drive coil 30 acts on the drive magnet 20 attached to the body 12 to cause oscillations of the body 12 which are measured by a signal induced in pickup coil 32 which is acted upon by pickup magnet 22. The period of oscillation of the body 12 is measured to determine the bulk density of the material within the body 12 in accordance with the above formulas.

In the preferred embodiment of the invention, the body 12 has an inside diameter of three inches and an overall length of 8 inches. The dimensions of the torsional springs 14, 16 were selected to resonate the mechanical mass of the system at from 90–100 Hz, corresponding to a period of from 0.011 – 0.010 seconds.

The preferred embodiment of the instrument 10 operates at $T_0 = 0.0973$ seconds. The value of $K'$ is 0.92 and the value of $\alpha$ from 0.87 to 0.95. The effective residence time varies from 4.2 minutes (for $\rho$ from 0 to 0.3 gm/cc) to 2.8 minutes (for $\rho$ from 0.3 to 0.6 gm/cc).

SERVO DRIVE SYSTEM

Figure 10:
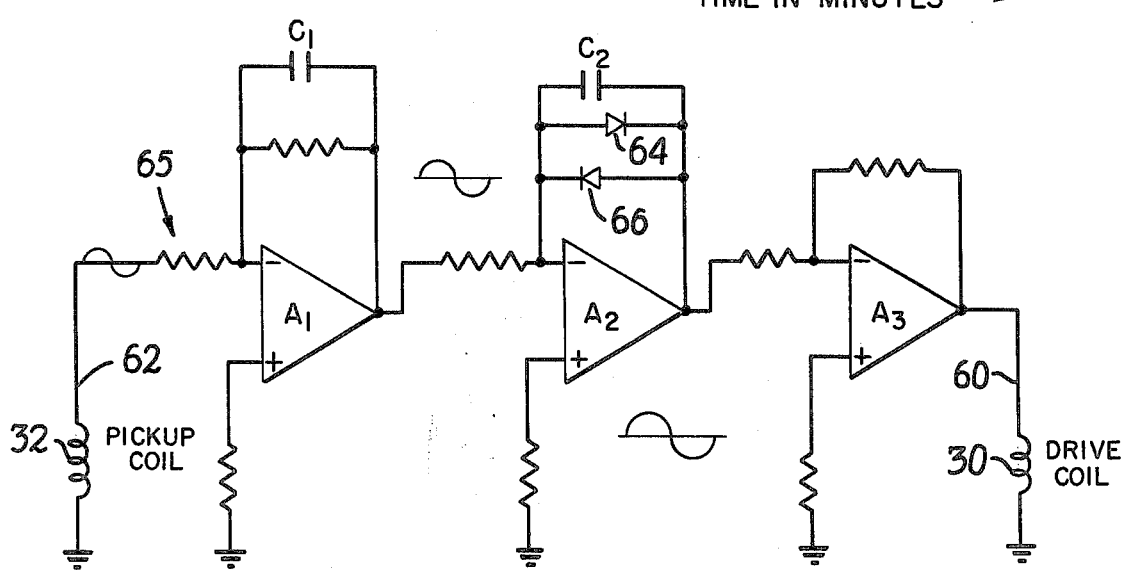
FIG. 10 is a schematic diagram of the servo drive circuitry used in conjunction with the instrument.

Referring generally to FIGS. 4 and 10, the instrument 10 is equipped with a servo drive circuit 65, including drive coil 30 and pickup coil 32. The coils 30, 32 convert the motion of the body 12 into an electrical signal and vice versa. The output of the pickup coil 32 is applied to the inverting input of an operational amplifier $A_1$ which operates as an inverting integrator. Amplifier $A_1$ shifts the phase of the pickup coil's output and drives operational amplifier $A_2$. Amplifier $A_2$ has a logarithmic response due to the feedback diodes 64, 66 connected between its output and input. The logarithmic response characteristic aids in stabilizing the operating point of the oscillating body 12. Feedback capacitor $C_2$ connected in parallel with the diodes 64, 66 causes an additional phase shift which, together with the mutual inductance between the pickup coil 32 and drive coil 30, serves to maintain oscillation through highly damped conditions, such as during startup.

READOUT

Readout for the instrument involves taking the difference between two large numbers, T and $T_0$. The output of the servo drive system 65 is passed through a readout circuit 71 (FIG. 8) including a frequency-to-voltage ($f/V$) converter 68 whose output is a filtered DC voltage directly proportional to frequency. The output of the $f/V$ converter 68 is applied to an analogue multiplier-divider ($m/d$) 70 whose transfer function is $10Z/x$. When $R_2 = \infty$, the output of the $m/d$ 70 is an output voltage directly proportional to the period of oscillation T. The output voltage, and a fixed voltage (derived by voltage divider $R_4$, $R_5$, and $R_6$) which equals the output voltage of the $m/d$ 70 when the body 12 is empty, corresponding to $T_0$, are then applied to the non-inverting and inverting inputs, respectively, of unity gain differential amplifier $A_4$. The output of $A_4$ is, therefore, proportional to $T - T_0$.

$R_3$ is selected to yield $Z = 1.0$ volts when the body 12 is empty, and $R_2$ is adjusted so the output of the $m/d$ 70 is increased sufficiently when $\rho = 1.00$ to compensate the output of amplifier $A_4$, for the missing $T + T_0$ term. This technique for introducing the $(T + T_0)$ is not exact, but over the range of interest ($\rho = 0.0$ to 0.60) yields readout data which agrees with theoretical values to greater than $\pm 0.001$ gm/cc. The output voltage of amplifier $A_4$, which is proportional to $(T - T_0)(T + T_0)$ is applied to the voltage divider formed by resistors $R_7$ and $R_8$ to introduce the $K'$ term of the equation. The output voltage, Vo, corresponds to the density, $\rho$, of the sample.

In operation, the instrument was found to have a temperature coefficient of $5 \times 10^{-4}$ units/° F. The change in output with temperature caused by the temperature coefficient is removed by using a temperature sensitive bridge whose active element is placed in the product stream. The output of the temperature sensitive bridge is introduced into the inverting input of amplifier $A_1$ of FIG. 10. The output of the $m/d$ is thereby temperature compensated, and the instrument was found to have a stability of greater than $\pm 0.001$ gm/cc over a temperature range of $\pm 20°$ F.

As shown in FIG. 9, the output of the density instrument 10 agrees with theoretical values up to $\rho = 0.33$ gm/cc. In the range of $\rho = 0.33 - 0.60$ gm/cc, the output differs from theoretical values in a predictable manner so that standard analogue techniques may be utilized to provide automatic correction.

Figure 11:
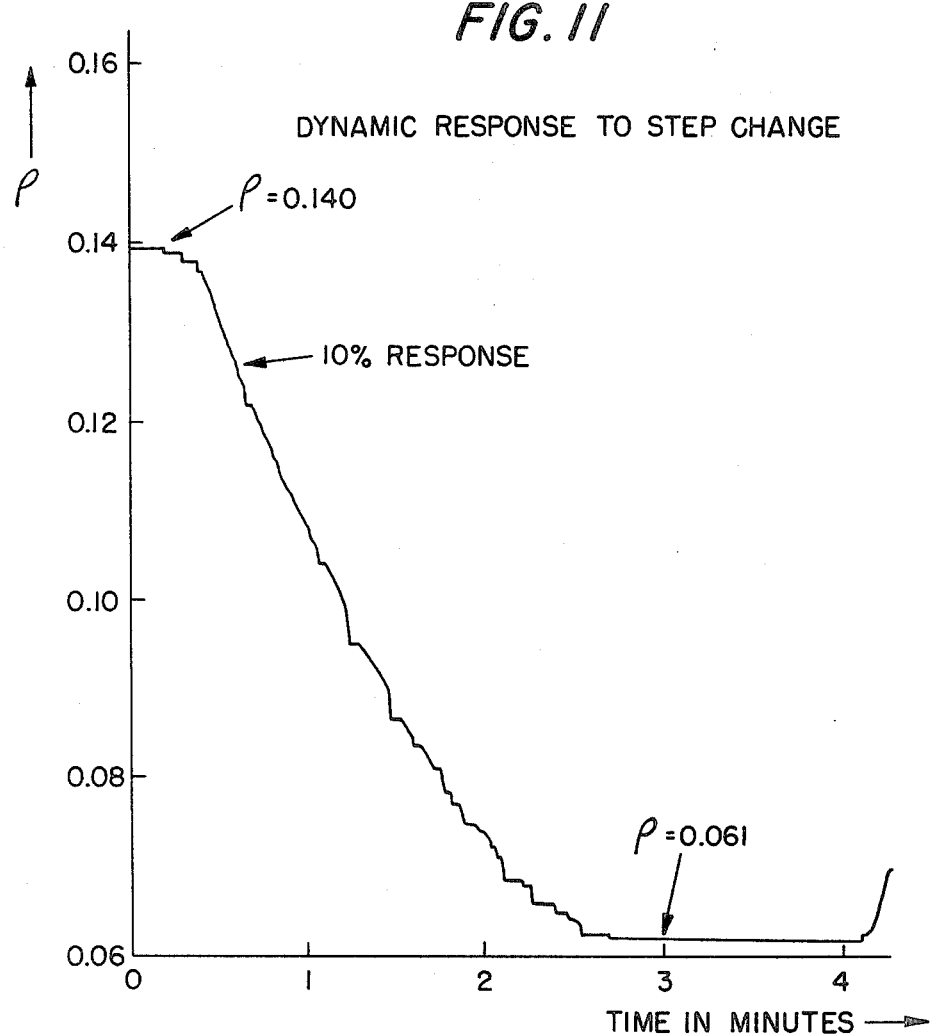
FIG. 11 is a graph showing the step change response of the instrument.

Referring generally to FIG. 11, a continuous recording of the response of the instrument 10 to a step change in $\rho$ is shown. The first 10% of the change is indicated within 45 seconds, and 100% of the step change is observable in less than 3 minutes.

I claim:

1. An instrument for measuring the bulk density of a powder comprising:
   a. a cylindrical body adapted to receive and discharge part of a stream of powder, said body being substantially open at the top and partially closed off at the bottom in order to restrict the flow of powder through said body causing a certain buildup of powder in said body;
   b. mounting means located adjacent the top of said body for pivotally suspending said body in a substantially vertical position so that the body acts like a pendulum, said mounting means being adapted to allow said body to oscillate with its natural period in a vertical plane about said mounting means;
   c. driving means for causing said body to oscillate with its natural period in said vertical plane;
   d. measuring means for determining the oscillation period of said body which represents the density of the material in the apparatus; and
   e. at least one spring located at said mounting means for generating a restoring force upon said body when said body is pivoted about said mounting means.

2. The instrument of claim 1 in which said driving means comprises at least one magnet attached to said body.

3. The instrument of claim 2 in which said driving means further comprises at least one drive electromagnet.

4. The instrument of claim 1 in which said measuring means comprises at least one pickup electromagnet adapted to have a voltage induced therein by at least one magnet mounted on said body.

5. The instrument of claim 4 in which said driving means comprises at least one magnet attached to said body.

6. The instrument of claim 5 in which said driving means further comprises at least one drive electromagnet.

7. The instrument of claim 6 further comprising servo drive means for inducing a voltage in said drive electromagnet in response to the voltage induced in said pickup electromagnet.

8. The instrument of claim 1 in which the top opening of said body is covered by a protective screen.

9. The instrument of claim 1 wherein said measuring means comprises an electronic circuit responsive to the frequency of oscillation of said body and whose output is a signal representative of the density of the material in said body.

10. The instrument of claim 1 wherein said spring is a first torsion spring.

11. The instrument of claim 10 wherein said spring further comprises a second torsion spring, said first and second springs being located on opposite sides of said body adjacent its top.

12. The instrument of claim 11 wherein said first and second torsion springs act as both said mounting means and said spring.

13. The instrument of claim 12 further comprising means for suspending said mounting means within a housing adapted to be attached to pipes conveying powdered product.

14. The instrument of claim 13 in which said housing is substantially cylindrical.

15. The instrument of claim 14 in which said means for suspending comprises an annular ring to which said torsion springs are attached, said annular ring adapted to be attached to the inside of said housing.

16. The instrument of claim 13 further comprising means for attaching said housing to said pipes.

17. The instrument of claim 16 wherein said means for attaching comprises flanges at the ends of said housing.

* * * * *